US010175314B2

(12) United States Patent
Mazurewitz et al.

(10) Patent No.: US 10,175,314 B2
(45) Date of Patent: Jan. 8, 2019

(54) NON-INVASIVE PROSTATE COIL FOR MR SYSTEMS WITH VERTICAL MAIN FIELD (71) Applicant: KONINKLIJKE PHILIPS N.V., Eindhoven (NL)

(72) Inventors: Peter Mazurewitz, Hamburg (DE); Christoph Leussler, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1001 days.

(21) Appl. No.: 14/405,800

(22) PCT Filed: May 27, 2013

(86) PCT No.: PCT/IB2013/054369
§ 371 (c)(1),
(2) Date: Dec. 5, 2014

(87) PCT Pub. No.: WO2013/182949
PCT Pub. Date: Dec. 12, 2013

(65) Prior Publication Data
US 2015/0177346 A1 Jun. 25, 2015

Related U.S. Application Data
(60) Provisional application No. 61/656,549, filed on Jun. 7, 2012.

(51) Int. Cl.
G01R 33/38 (2006.01)
A61B 5/055 (2006.01)
(Continued)

(52) U.S. Cl.
CPC ............. *G01R 33/38* (2013.01); *A61B 5/055* (2013.01); *A61B 5/4381* (2013.01); *G01R 33/34* (2013.01);
(Continued)

(58) Field of Classification Search
USPC .......................... 324/300–322; 600/407–435
See application file for complete search history.

(56) References Cited

U.S. PATENT DOCUMENTS 5,144,241 A 9/1992 Oppelt
5,307,814 A 5/1994 Kressel
(Continued)

FOREIGN PATENT DOCUMENTS

CN 1785119 A 6/2006
EP 0845683 A1 6/1998
(Continued)

*Primary Examiner* — Patrick Assouad
*Assistant Examiner* — Tiffany Fetzner (57) ABSTRACT An inductively coupled magnetic resonance local prostate radio frequency coil (10) includes at least two connected electrically conductive loops (50) and an interface device (80). The at least two connected electrically conductive loops (50) are tuned to receive magnetic resonance radio frequency signal components along an axis of a subject disposed in a main magnetic field (B0) orthogonal to the axis of the subject (i.e. an open MRI system having a vertical magnetic field) and generate one or more currents indicative of the received magnetic resonance signal components. The interface device (80) connected to the at least two conductive loops transmits measures of the one or more currents to a signal processing system.

19 Claims, 10 Drawing Sheets (51) Int. Cl.
*G01R 33/34* (2006.01)
*G01R 33/36* (2006.01)
*G01R 33/3415* (2006.01)
*A61B 5/00* (2006.01)

(52) U.S. Cl.
CPC ....... *G01R 33/34084* (2013.01); *G01R 33/36* (2013.01); *G01R 33/3415* (2013.01); *G01R 33/34053* (2013.01); *G01R 33/3678* (2013.01); *G01R 33/3692* (2013.01); *G01R 33/3806* (2013.01)

(56) References Cited

U.S. PATENT DOCUMENTS

| | | | |
|---|---|---|---|
| 6,051,974 A | 4/2000 | Reisker | |
| 6,836,117 B2 * | 12/2004 | Tamura | G01R 33/3678 324/318 |
| 7,450,984 B2 * | 11/2008 | Engelhard | G01R 33/341 324/318 |
| 7,646,199 B2 * | 1/2010 | Dannels | G01R 33/34007 324/318 |
| 7,701,209 B1 | 4/2010 | Green | |
| 8,089,281 B2 | 1/2012 | Zhai et al. | |
| 8,188,740 B2 | 5/2012 | Ninomiya et al. | |
| 8,598,880 B2 * | 12/2013 | Dalveren | G01R 33/34084 324/318 |
| 9,002,431 B2 * | 4/2015 | Jones | A61B 5/055 2/69 |
| 9,146,290 B2 * | 9/2015 | Ylihautala | G01R 33/288 |
| 2002/0013526 A1 | 1/2002 | Su | |
| 2002/0169375 A1 | 11/2002 | Nabetani | |
| 2003/0016017 A1 | 1/2003 | Reykowski | |
| 2003/0197508 A1 * | 10/2003 | Tamura | G01R 33/3678 324/318 |
| 2004/0002648 A1 * | 1/2004 | Engelhard | G01R 33/341 600/422 |
| 2008/0211498 A1 * | 9/2008 | Dannels | G01R 33/34007 324/309 |
| 2009/0082664 A1 | 3/2009 | Schilling | |
| 2012/0286788 A1 * | 11/2012 | Ylihautala | G01R 33/288 324/322 |
| 2012/0293174 A1 * | 11/2012 | Taracila | G01R 33/34084 324/318 |
| 2013/0137969 A1 * | 5/2013 | Jones | G01R 33/34007 600/421 |
| 2014/0167758 A1 | 6/2014 | Sambandamurty et al. | |
| 2015/0173678 A1 * | 6/2015 | Jones | G01R 33/34007 600/421 |
| 2015/0177346 A1 * | 6/2015 | Mazurewitz | G01R 33/34084 324/309 |

FOREIGN PATENT DOCUMENTS

| | | |
|---|---|---|
| JP | 2003024301 A | 1/2003 |
| JP | 2006014823 A | 1/2006 |
| RU | 2192165 C1 | 11/2002 |
| WO | 2010056911 A1 | 5/2010 |

* cited by examiner

Conventional MR Scanner with Horizontal Main Field

MRI-systems with vertical main field

PRIOR ART

FIGURE 2

FIGURE 3A — Coil design 1

FIGURE 3B — Coil design 2

FIGURE 3C — Coil design 3

NON-INVASIVE PROSTATE COIL FOR MR SYSTEMS WITH VERTICAL MAIN FIELD

CROSS-REFERENCE TO PRIOR APPLICATIONS

This application is the U.S. National Phase application under 35 U.S.C. § 371 of International Application No. PCT/IB2013/054369, filed on May 27, 2013, which claims the benefit of U.S. Provisional Patent Application No. 61/656,549, filed on Jun. 7, 2012. These applications are hereby incorporated by reference herein.

The following relates generally to magnetic resonance arts. It finds particular application in conjunction with local radio frequency (RF) resonance coils for open or vertical field magnet systems, and will be described with particular reference thereto. However, it will be understood that it also finds application in other usage scenarios and is not necessarily limited to the aforementioned application.

MR systems produce high resolution 3D images of human anatomy. A subject undergoing a magnetic resonance (MR) procedure such as an MR imaging procedure is positioned on a patient support within the main magnetic field ($B_0$), which is static. RF field ($B_1$) pulses are applied at a magnetic resonance frequency to excite resonance in dipoles of the subject. Within the main field is a whole body coil which generates RF pulses in accordance with a selected imaging protocol. In some imaging procedures, local coils are placed next to the body in various locations to receive RF resonance signal and/or to generate RF pulses. When used in transmit mode, the local coils focus RF pulses on a specific body part or location. The local coils receive the weak magnetic resonance decay RF signals close to the body and retransmit the received signals to a receiver. The magnetic field direction of the received RF field is orthogonal to the magnetic field direction of the main field ($B_0$). The received RF data is reconstructed into one or more images.

Bore-type MR systems include a bore surrounded by a main magnet coil which generates the static field ($B_0$) horizontally along an axis centered in the bore. The axis of a subject is typically parallel to the axis of the static field. $B_1$ fields are applied which are orthogonal to the $B_0$ static field. Local coils used with traditional systems receive the orthogonal RF field components typically oriented up and down or side to side. The local coils are designed to conform to the outer surface of various body parts of the subject in a supine position passing through the bore and receive signals which are orthogonal to the static field. Open MR systems which are more open and less claustrophobic use a main field which is orthogonal to the axis of the subject such as a vertical main field. The imaged subject typically is disposed in a supine position between an upper and lower surface of the vertical main imaging system. However, with the vertical reorientation of the static field, local coils designed to operate with a horizontal static field in the up and down orientation are no longer orthogonal to the vertical main field, although they still conform to the outer surface of the body. Local coils traditionally used with horizontal main field systems do not measure the orthogonal RF fields to the vertical main field. One notable example is coils used for imaging the prostate region.

An area of interest in magnetic resonance imaging is the prostate. In traditional horizontally oriented main fields, a local coil such as an abdominal local coil can be used to image the prostate area. MR imaging can be used for MR guided biopsies. MR guided biopsies involve inserting a needle guide through the rectum next to the patient prostate. An abnormal area identified in images is targeted and the imageable needle guide guides the needle to the targeted tissue to take biopsies of the targeted tissue. The local coil used during biopsies includes open access for surgical instruments to perform the biopsies.

The following discloses a new and improved dedicated non-invasive prostate coil for MR systems with a vertical main field which addresses the above referenced issues, and others.

In accordance with one aspect, an inductively coupled magnetic resonance local prostate radio frequency coil includes at least two connected electrically conductive loops and a an interface device. The at least two connected electrically conductive loops are tuned to receive magnetic resonance radio frequency signal components along an axis of a subject disposed in a main magnetic field ($B_0$) orthogonal to the axis of the subject and generate one or more currents indicative of the received magnetic resonance signal components. The interface device connected to the at least two conductive loops transmits measures of the one or more currents to a signal processing system.

In accordance with another aspect, a method for imaging a region with magnetic resonance includes positioning a subject on a patient support with at least two connected electrically conductive loops tuned to receive magnetic resonance radio frequency signal components along an axis of the subject disposed in a main magnetic field ($B_0$) orthogonal to the axis of the subject and generate one or more currents indicative of the received magnetic resonance signal components. Magnetic resonance is excited in the subject and measures of the generated one or more currents are transmitted. The transmitted measures of the generated one or more currents are received. One or more images from the received measures of the generated one or more currents are reconstructed.

In accordance with another aspect, a magnetic resonance local radio frequency coil includes at least two electrically conductive loops and an interface device. The at least two electrically conductive loops are tuned to receive magnetic resonance radio frequency signals and connect along a length between the thighs of a subject and surround an axial portion of the subject. The interface device connects to the at least two electrically conductive loops and transmits measures of the received magnetic resonance radio frequency signals.

One advantage is a local coil which operates in a main field orthogonal to the axis of the subject.

Another advantage resides in detecting of field components that are parallel to an axis of a subject.

Another advantage resides in open access of the coil design.

Another advantage resides in multiple modes in which the coil can operate.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

Figure 1A:
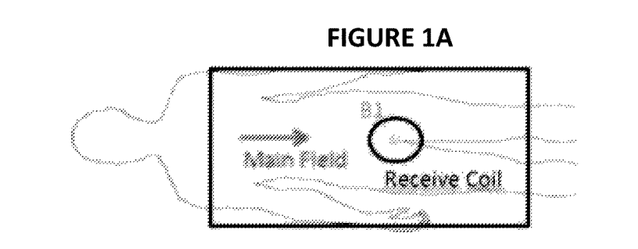
FIGS. 1A-D schematically illustrates the orientation of the main field and a local receive coil in a horizontal main field and a vertical main field.
Figure 1B:
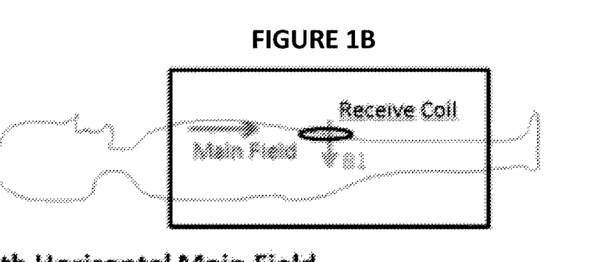
Figure 1C:
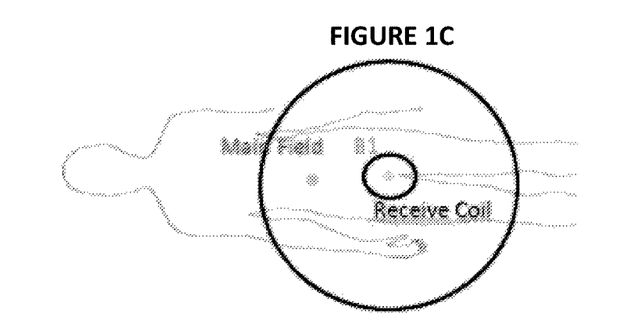
Figure 1D:
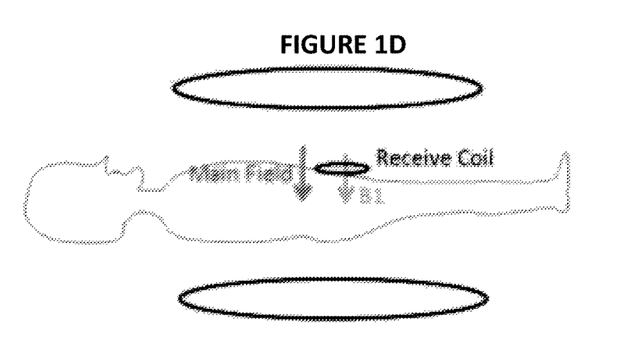

In FIGS. 1A and 1B, the main field orientation to the patient is shown for a conventional MR scanner with a horizontal main field ($B_0$). In FIG. 1A, a top view is shown with the bore represented as a rectangular area and a local coil shown as a loop coil. The direction of the $B_0$ field is from the axis from the head to the feet, and the direction of the RF field or $B_1$ field is into the patient. FIG. 1B shows the same orientation from a side view which illustrates the $B_1$ field orthogonal to the $B_0$ field with a loop coil disposed on the surface of the patient in the groin area. FIGS. 1C and 1D contrast the same local coil and patient orientation in a MR scanner with a vertical main field ($B_0$). The $B_0$ field in FIGS. 1C and 1D is parallel to the $B_1$ field of the local coil and the direction is into the patient. The side view shows the parallel relationship between the $B_0$ and $B_1$ fields which render the local coil insensitive to the $B_1$ field.

Figure 2:
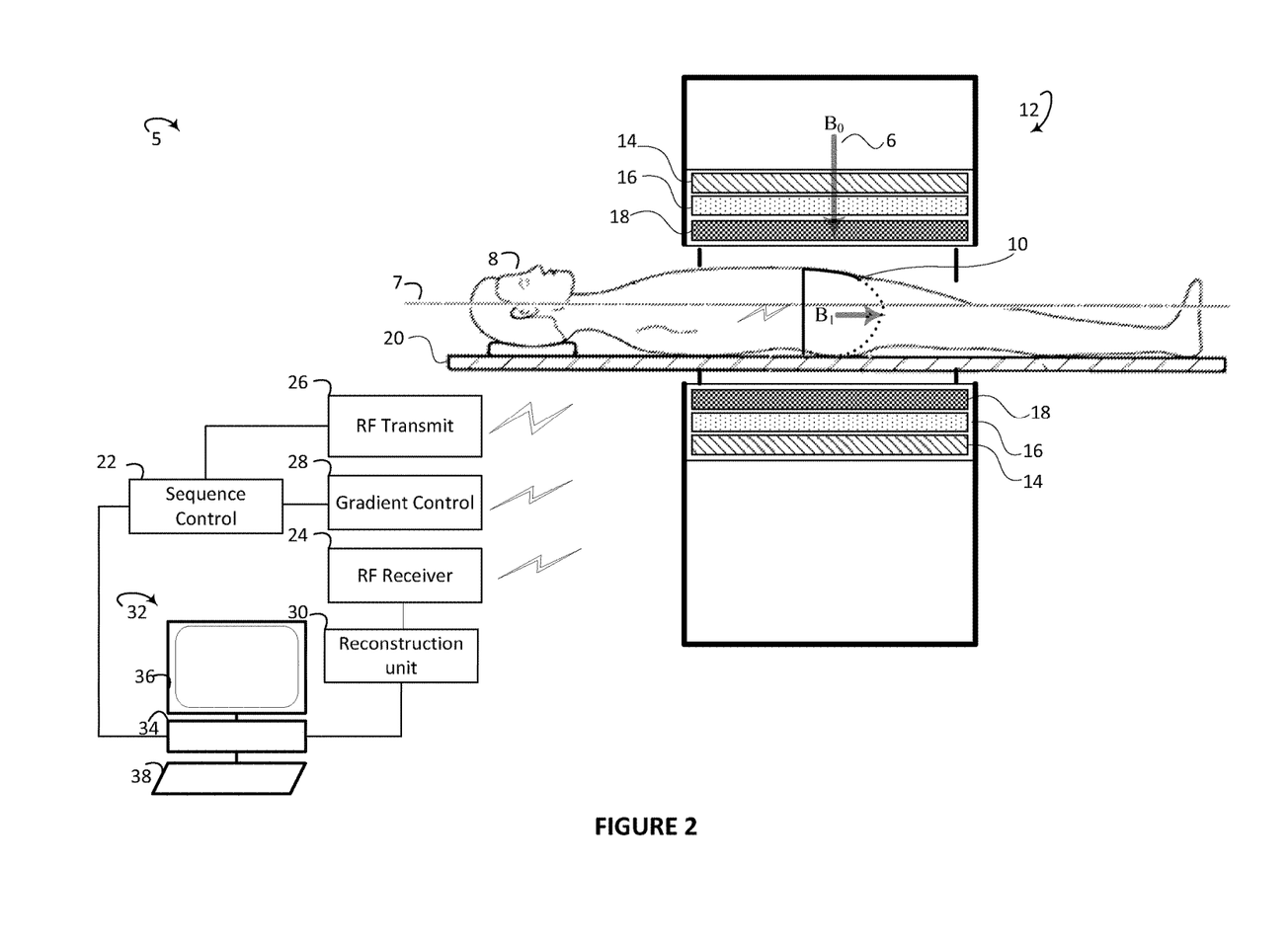
FIG. 2 schematically illustrates one embodiment of a vertical main MR system with a dedicated local prostate coil.

With reference to FIG. 2, an embodiment of MR system 5 with a static $B_0$ main field 6 orthogonal to an axis 7 of a subject 8, and a local prostate coil 10 are diagrammatically illustrated. The system 5 includes a MR scanner 12. The MR scanner 12 includes a main magnet 14 whose poles generate the static main field ($B_0$) 6 such as a vertical main field. The MR scanner further includes one or more gradient coils 16 for applying gradient fields and one or more RF coils 18 which generate RF pulses to excite magnetic resonance in the subject 8 and which, in some embodiments can pick-up resonance signals from the subject. The MR scanner 12 includes open designs such as a panorama or "C" type open scanner. The subject is supported on a patient support 20 such as a horizontal bed or couch within a vertical main scanner. The system includes a sequence controller 22 and a Radio Frequency (RF) receiver unit 24. The sequence controller controls the operation of the imaging sequence which includes a RF transmitter unit 26 controlling the operation of the RF coils 18 and a gradient controller 28 controller the operation of the gradient coils 16. The communication between the controlling unit and the corresponding coils can be wireless or wired. The RF transmitter unit 26 works cooperatively with the local coil 10 when configured as a transmit/receive coil. The RF receiver 24 receives RF data from local coil indicative of the magnetic resonance excited in the tissue of the subject. The RF data can be communicated between the local coil and the RF receiver wirelessly or a wired connection. With a wireless connection, power is used from an induced current or a separate power source to transmit RF data. With a wired connection, the wire can optionally supply power for amplification and carry the resonance signal. A reconstruction unit 30, such as a processor, receives RF data from the RF receiver 24 and reconstructs one or more images from the received data.

The local prostate coil 10 includes at least two connected electrically conductive loops tuned to receive orthogonal components of magnetic resonance radio frequency signals which orthogonal components are orthogonal to the $B_1$ field, e.g. along the axis of the subject and transverse to the subject. The local prostate coil further includes an interface device which communicates between the local coil and the RF receiver. The resonance signals inductively generate one or more currents indicative of the magnetic resonance. The conductive loops connect as they pass between the upper thighs of the subject near the groin area. The conductive loops act as a local receive coil for tissue in the prostate region of the subject. When a prostate coil 10 is a receive only local coil, the RF pulse is transmitted by the whole body coil. Optionally, with a power source and a controller, the conductive loops of the local coil can also operate as a transmit and receive coil which focus magnetic resonance in the prostate tissue.

The system 5 includes a workstation 32. The workstation 32 includes an electronic processor or electronic processing device 34, a display 36 which displays the images, menus, panels, and user controls, and the at least one input device 38 which inputs the healthcare practitioner selections. The workstation 32 can be a desktop computer, a laptop, a tablet, a mobile computing device, a smartphone, and the like. The input device can be a keyboard, a mouse, a microphone, and the like.

The various units or controllers 22, 24, 26, 28, 30 are suitably embodied by an electronic data processing device (s), such as the electronic processor or electronic processing device 34 of the workstation 32, or by a network-based server computer operatively connected with the workstation 32 by a network, or so forth. Moreover, the disclosed reconstruction and system operation are suitably implemented as a non-transitory storage medium storing instructions (e.g., software) readable by an electronic data processing device and executable by the electronic data processing device to perform the disclosed reconstruction and system operation.

The display 36 or display device as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Figure 3A:
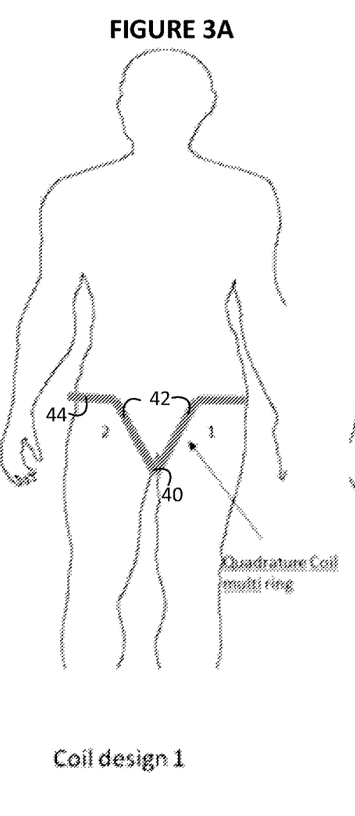
FIGS. 3A-C diagrammatically illustrates three embodiments of a dedicated local prostate coil.
Figure 3B:
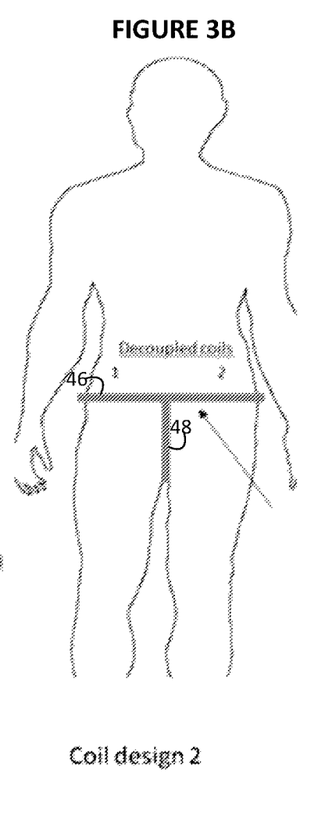
Figure 3C:
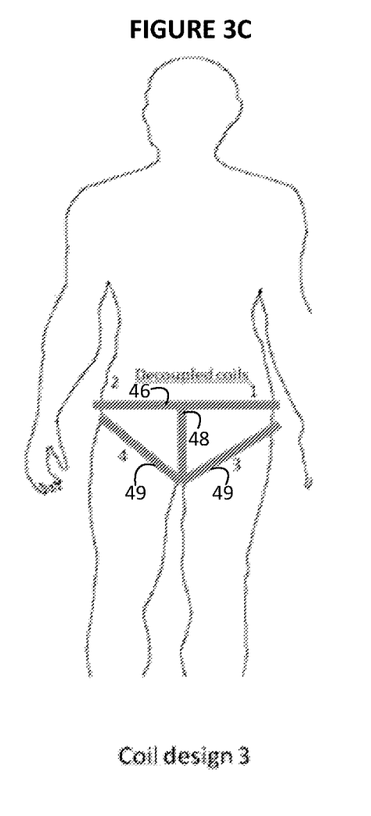

With reference to FIGS. 3A-3C, three different non-invasive embodiments of the local magnetic resonance prostate coil where the electrically conductive coil length(s) and the electrically conductive coil loop(s) create the formation of an underwear shape, or a thong shape, or a shape combining the underwear and thong shape, around the torso of a subject that is adjacent to the pelvic area of the subject are shown. In FIG. 3A, the conductive loops are arranged in either an underwear shape, or a thong shape and are connected at connection 40 between the upper thighs of the subject and separate diagonally away 42 from the pubic region over the hip joint toward the waist of the subject. At the waist of the subject, the conductive loops pass around the waist 44 from the front of the subject to the back of the subject near the body surface. The direction in the back over the buttocks region mirrors the direction in the front. The conductive loops are sized to fit over each of the upper thigh and buttocks of the subject and extend over the waist of the subject. The thickness of the conductive loops provides an open access to the prostate region. The design of FIG. 3A tunes the non-invasive local magnetic resonance prostate coil to either decouple the loops or operate as a quadrature coil. The non-invasive local magnetic resonance coil can functionally operate in both of these two modes.

In FIG. 3B, a thong shaped configuration is shown wherein the conductive loops are sized such that a conductive band 46 surrounds a waist of the subject, and a length 48 passes vertically between the upper thighs of the subject and connects front and back to the conductive band. The conductive loops share the length that passes between the upper thighs and separate at the juncture of the length to the band which surrounds the waist. The thickness of the conductive loops provides an open access to the prostate region. The design of FIG. 3B tunes the non-invasive local magnetic resonance prostate coil to either decouple the loops, or operate as a quadrature coil. The non-invasive local magnetic resonance coil can functionally operate in both of these two modes.

FIG. 3C illustrates an embodiment which includes four conductive loops that are arranged to create or form a structure combining the underwear or thong shape, of FIG. 3A, with the thong shape of FIG. 3B, and which extends around the torso of a subject that is adjacent to the pelvic area of the subject. The design of FIG. 3C adds two loops 49 similar to the design illustrated in FIG. 3A to the design illustrated in FIG. 3B. The additional loops connect to the length which passes through the upper thighs of the subject. Each additional loop encircles the upper thigh angled toward waist of the subject. The additional loops generally pass over the hip joint. The thickness of the conductive loops provides an open access to the prostate region. The design of FIG. 3C tunes the non-invasive local magnetic resonance prostate coil to decouple the four loops.

Figure 4:
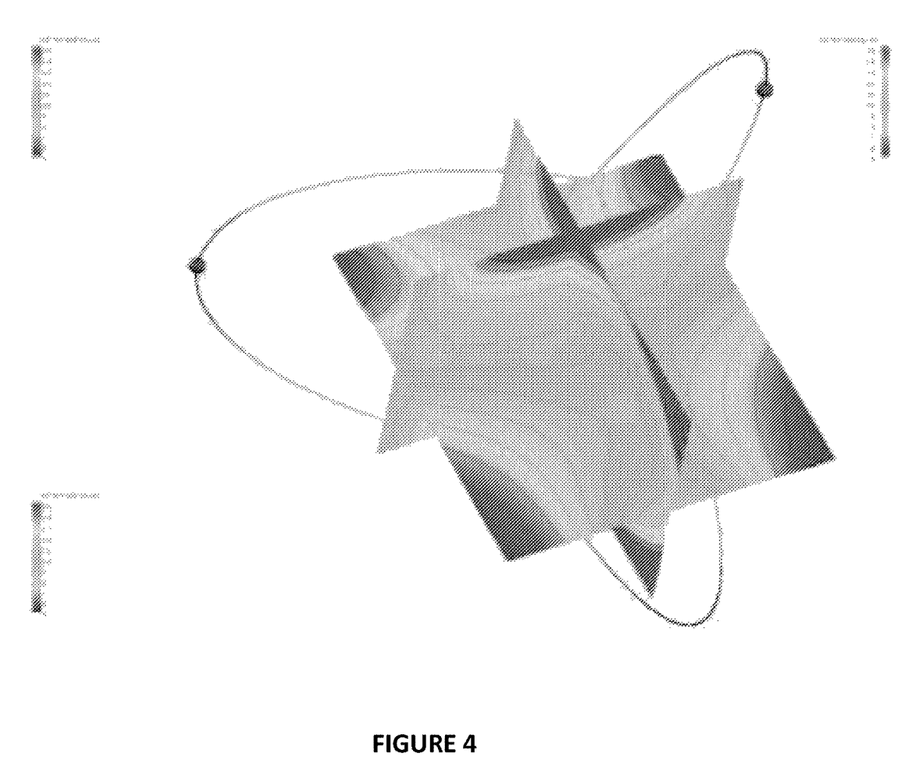
FIG. 4 in a 3D graph depicts the RF field sensitivity in one embodiment of the local prostate coil.

With reference FIG. 4, a 3D graph depicts the RF field sensitivity based on the local prostate coil design illustrated in FIG. 3B. The darken region of the graph shows a darken region where the sensitivity is the greatest. The darken region is illustrated in a contour of a volume which represents a cross. The region shown with the greatest sensitivity corresponds to the prostate region in the subject. The darken region is close to the conductive loops. The sensitivity is highest closest to the conductive loops.

Figure 5A:
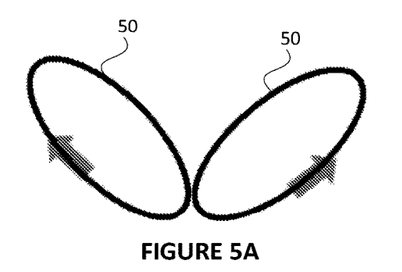
FIGS. 5A-D graphically illustrates operating modes of local prostate coil embodiments.
Figure 5B:
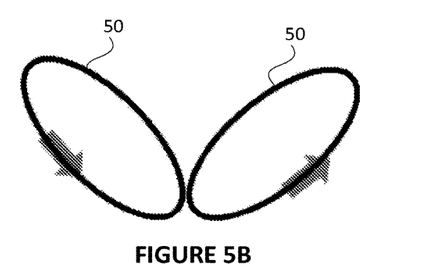
Figure 5C:
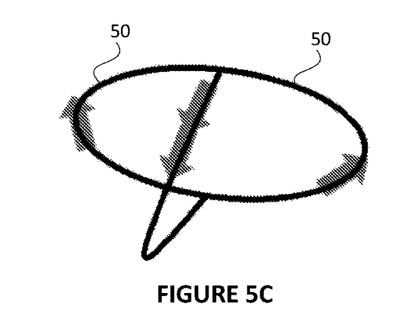
Figure 5D:
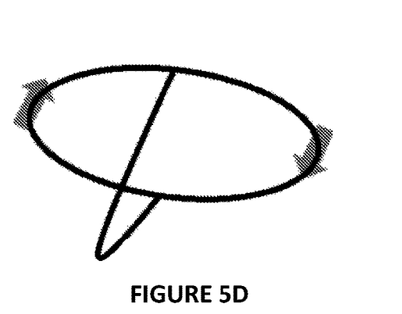

FIGS. 5A-D graphically illustrates operating modes of the local prostate coil embodiments. FIGS. 5A and 5B illustrate the two operating modes of the local prostate coil depicted in FIG. 3A. In FIG. 5A current flows in each coil or conductive loop 50 in opposite directions around the upper thigh/hip joint such as one flowing clockwise and one flowing counter clockwise. This mode has good sensitivity to transverse resonance signal components. In a second operating mode, FIG. 5B shows the current flowing in the same direction in each conductive loop 50, either both clockwise or both counter-clockwise. This mode has good sensitivity to axial resonance signal components. In the quadrature mode, the coils are tuned concurrently to both modes. FIGS. 5C and 5D illustrate two operating modes of the coil depicted in FIG. 3B. In FIG. 5C, current flows in opposite directions around each side of the waist of the subject and in a common direction between the legs of the subject. The two conductive loops 50 share the length between the legs as a common path. This mode has sensitivity to transverse resonance signal components. FIG. 5D depicts a second mode of the same coil with current flowing around the waist of the subject and not between the legs of the subject. A portion of each conductive loop 50 forms a single conductive loop. This mode has good sensitivity to axial resonance signal components. In the quadrature mode, the coils are tuned concurrently to both modes. The current paths and operating modes of FIG. 3C are the combination of the current paths and operating modes combined from FIGS. 5A-D. This provides a plurality of loops with different sensitivities which are amenable to parallel imaging techniques.

Figure 6A:
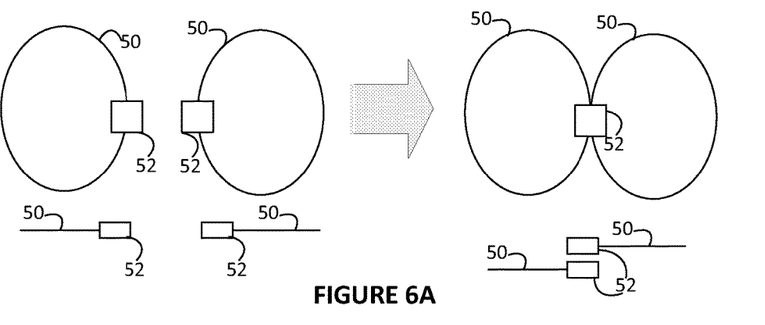
FIGS. 6A-C diagrammatically illustrates the components of embodiments of the local prostate coil.
Figure 6B:
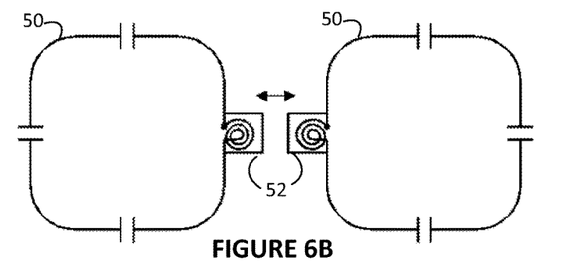
Figure 6C:
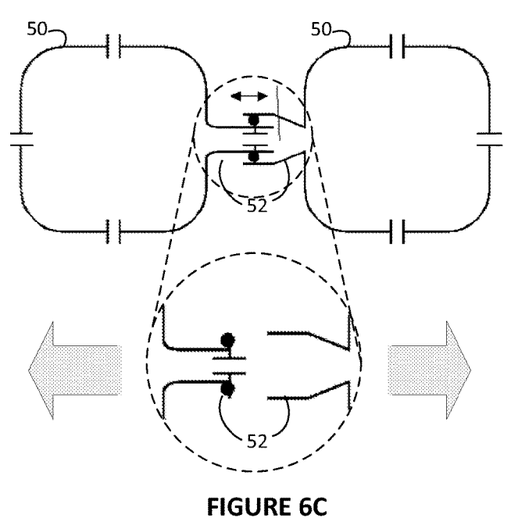

FIGS. 6A-C diagrammatically illustrates the components of another embodiment of the local prostate coil with reference to FIG. 3A. FIG. 6A shows two views of the local coil. The two conductive loops 50 connect together with a decoupling system. The decoupling system includes the two loops and each loop includes a connection device 52. The connection device 52 includes an inductive loop or a capacitive network for decoupling of both conductive loops. The connection device 52 includes portions which overlap and connect. FIG. 6B shows an embodiment with the connection device 52 which includes integrated flat transformers. In FIG. 6C, an embodiment of the local coil includes a connection device 52 which connect using springs with galvanic contact. The conductive loops 50 with the connection device separate or detach to improve workflow. The connection device can include the interface device which communicates between the local coil and the RF receiver.

Figure 7A:
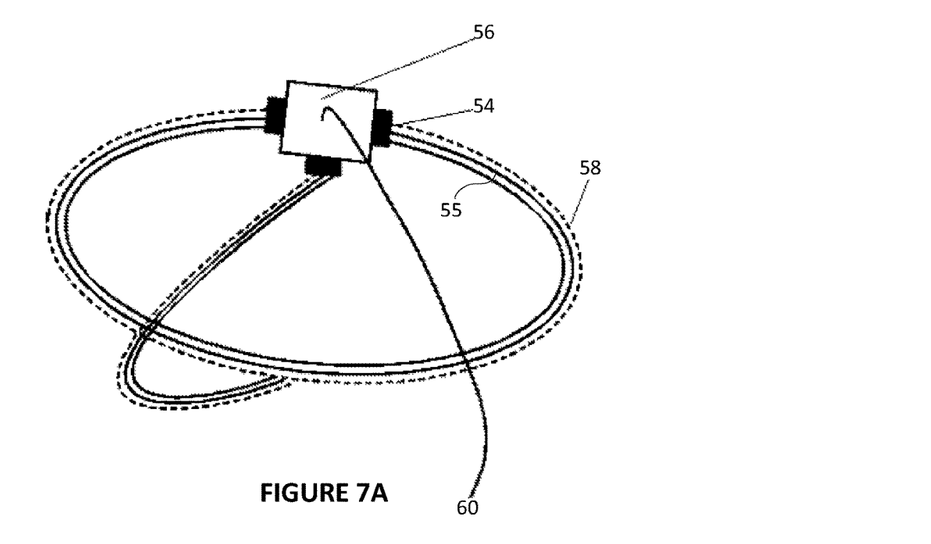
FIGS. 7A-B diagrammatically illustrates the components of another embodiment of the local prostate coil.
Figure 7B:
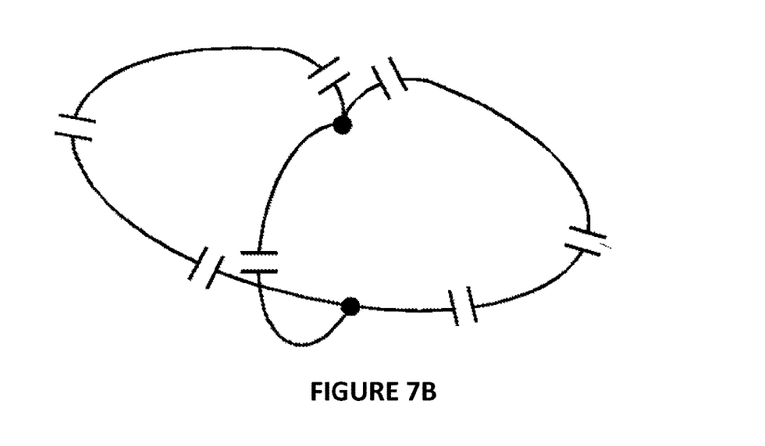

FIGS. 7A-B diagrammatically illustrates the components of an embodiment of the local prostate coil with reference to FIG. 3B. In FIG. 7A a connector 54 connects a length of conductive material 55 to a connection device 56. The connector 54 is an open/close type connector for improved workflow. The length of conductive material forms the conductive loop when connected to the connection device 56. The connection device 56 includes integrated detune electronics, an analog to digital converter, and an interface device. An optional disposable sleeve 58 covers the length of conductive material 55 to protect against bacteria, blood, etc. during interventional treatment. The connector 54 disconnects from the connection device 56 to install and de-install the protective sleeve 58. A connecting optical fiber 60 connects the interface device within the connection device 56 to the RF receiver and transmits the received RF data. FIG. 7B shows schematically the arrangement of the conductor pattern with tuning capacitors.

Figure 8A:
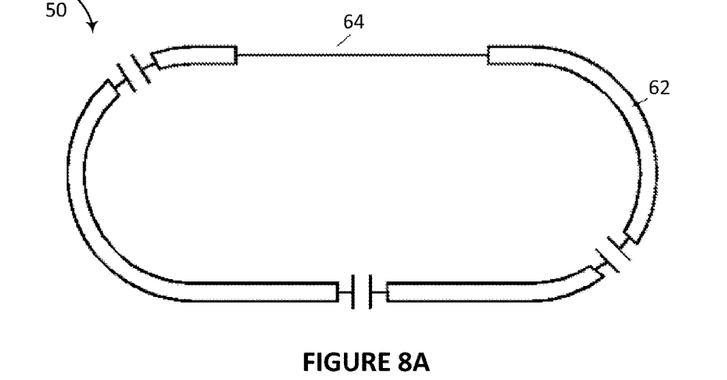
FIGS. 8A-B diagrammatically the components of one embodiment of the local prostate coil operating with High Frequency Ultrasound.
Figure 8B:
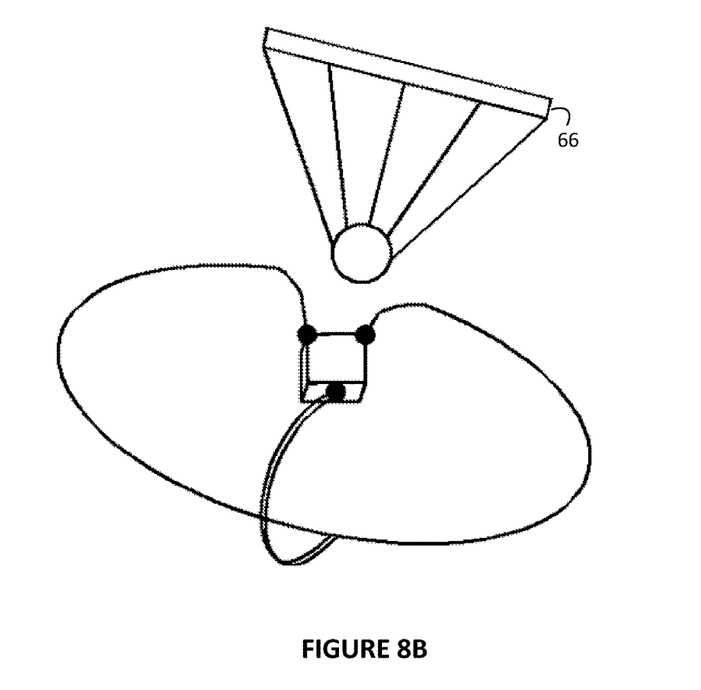

In FIGS. 8A-B, the components of one embodiment of the local prostate coil operating with High Frequency Ultrasound (HIFU) are diagrammed. With reference to FIG. 8A, the conductive loop 50 includes thin copper strips 62 or wire 64 for compatibility with high frequency ultrasound or positron emission tomography (PET). With reference to FIG. 8B, the compatibility of the open design of the local coil such as the embodiment with reference to FIG. 3A is shown with a HIFU emitter 66. The conductor arrangement with the open design provides openings such that no reflections of the HIFU beam occur from the local coil.

Figure 9A:
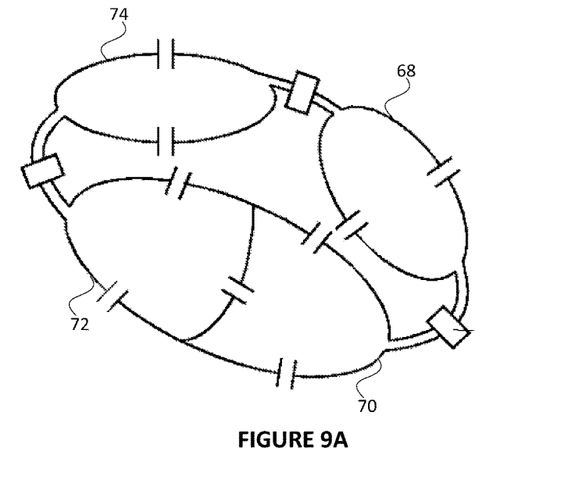
FIGS. 9A-B diagrammatically the components of another embodiment of the local prostate coil.
Figure 9B:
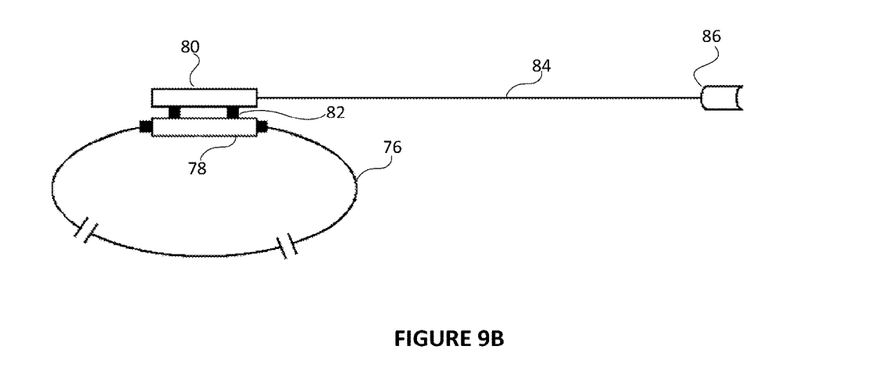

With reference to FIGS. 9A-B, the components of another embodiment of the local prostate coil are diagrammed. FIG. 9A shows the schematic arrangement of components of the local coil design with reference to FIG. 3C. The local coil design includes three connection devices with an arrangement of capacitors to operate the four decoupled conductive loops 68, 70, 72, 74. FIG. 9B shows a disposable conductive loop or coil 76 with connection device 78 and detune electronics. Disposable coils 76 are employed with therapy systems. A separate interface device 80 includes an analog to digital conversion and connects via a connector 82 to the disposable coil 76. The interface device measures the one or more currents induced by the magnetic resonance and transmits the one or more measures. An optical fiber 84 connects to the interface device 80 and to a connector 86. The optical fiber 84 carries the transmitted RF data from the interface device to the RF receiver.

Figure 10A:
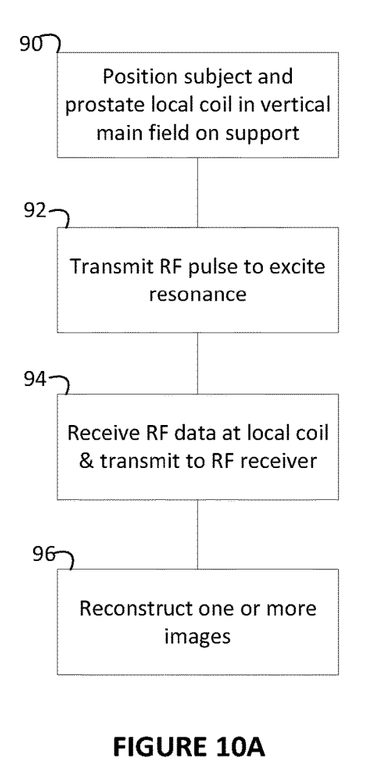
FIGS. 10A-B flowcharts methods of using different embodiments of the local prostate coil as a transmit/receive and receive only local RF coil.

With reference to FIG. 10A, the method of operating the receive only local prostate in one embodiment is flowcharted. In a step 90, the local prostate coil is fitted to the subject and the subject and coil are positioned in the main field of the MR scanner. The axis of the main field and the axis of the subject are orthogonal. The subject is supported by the support. Positioning the subject includes positioning the prostate region in the imaging region of the magnetic resonance system 12.

In a step 92, the sequence controller causes the RF coils 18 to transmit the RF pulses which excites and manipulates magnetic resonance in the prostate tissue of the subject. As the induced magnetic resonance in the subject decays, weak RF magnetic resonance signals are generated. The magnetic resonance signals induce one or more currents in the tuned local prostate coil. The local prostate coil is tuned to receive RF signals orthogonal to the main field. More specifically when tuned to the quadrature mode, the coils receive orthogonal magnetic resonance signal components transverse to the vertical magnetic field. In a parallel imaging mode the four loops of the FIG. 3C embodiment are individually tuned to form different sensitivities to generate four lines of k-space concurrently. The local prostate coil measures the induced currents and transmits the measures to the RF receiver. The sensitivity of the coil is optimized for the prostate region tissue.

The measures of the RF signals are received by the RF receiver 24 in a step 94. The received measures are transmitted to the reconstruction unit 30 which reconstructs the RF signals into one or more images in a step 96. The reconstruction unit uses the configuration of the local coil, the mode of operation, and the measured currents associated with each RF pulse to reconstruct the images. The images can then be used to control therapy with HIFU, a radiation beam, and the like or to guide a biopsy or other invasive procedure.

Figure 10B:
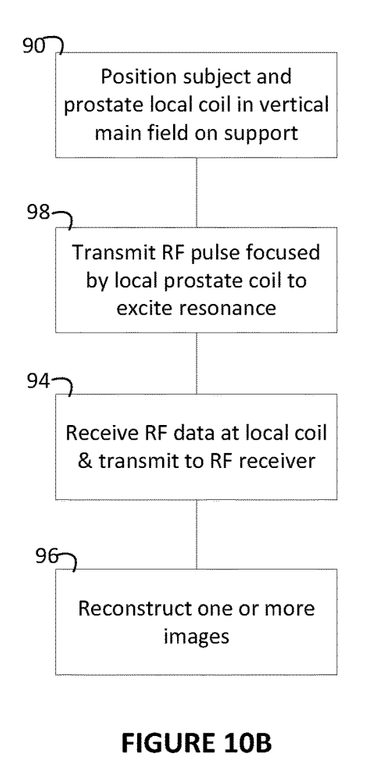

With reference to FIG. 10B, the method of operating the transmit/receive local prostate in one embodiment is flowcharted. The method modifies the embodiment flowcharted in FIG. 10A with a step 98. The RF pulse generated in a step 92 are modified in a step 98, where the RF pulses generated by the whole body coil are further focused by RF pulses generated by the local coil which focus the magnetic resonance in the prostate tissue. Once the pulses are generated, the local prostate coil switches to operate as a receive only coil to measure the magnetic resonance in a step 94 similar to the corresponding step in FIG. 10A.

The open designs of the various embodiments of the local prostate coil provide access with surgical instruments typically used to take biopsies of prostate tissue. The thickness of the conductive loops and the orientation provide openings and freedom of movement for both the subject and the healthcare practitioner performing the biopsy.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A non-invasive magnetic resonance local radio frequency prostate coil that is utilized in imaging the upper thighs and pelvic area of a subject comprising:
    at least two electrically conductive loops which are:
        1) tuned in order to receive magnetic resonance radio frequency signal components along an axis of a subject disposed in a main magnetic field (Bo) orthogonal to the axis of the subject in the main magnetic field (Bo); and
        2) generate one or more currents indicative of the received magnetic resonance signal components;
    wherein the at least two electrically conductive loops are also:
        a) detachably connected to one another via an integrated flat transformer;
        b) disposable or sheathed in a disposable sleeve;
        c) arranged in either an underwear shape, or a thong shape or a combination of an underwear shape and a thong shape;
        d) wrap around a torso of the subject adjacent the pelvic area of the subject, with a front and a back, connected between the upper thighs of the subject,
    an interface device connected to the at least two connected electrically conductive loops; and
    wherein the interface device is configured to transmit measures of the one or more currents indicative of the received magnetic resonance signal components into a signal processing system when the non-invasive magnetic resonance local radio frequency prostate coil is utilized.

2. The non-invasive magnetic resonance local radio frequency prostate coil according to claim 1, wherein the interface device couples the at least two connected electrically conductive loops in quadrature using at least one of a capacitive network of the connection device such that two orthogonal magnetic resonance signal components that are orthogonal to the main magnetic field are received by the at least two connected electrically conductive loops.

3. The non-invasive magnetic resonance local radio frequency prostate coil according to claim 1, wherein portions of each of the at least two connected electrically conductive loops connect and form a single conductive loop using a length of each electrically conductive loop.

4. The non-invasive magnetic resonance local radio frequency prostate coil according to claim 1, wherein the at least two connected electrically conductive loops are each sized in order to fit over each of an upper thigh of the subject.

5. The non-invasive magnetic resonance local radio frequency prostate coil according to claim 1, wherein the at least two connected electrically conductive loops are connected along a length which passes between the upper thighs of the subject.

6. The non-invasive magnetic resonance local radio frequency prostate coil according to claim 2, further including: a connector device configured to detachably connect the two additional electrically conductive loops with the electrically conductive coil length.

7. The non-invasive magnetic resonance local radio frequency prostate coil according to claim 6, wherein the connector device includes a flat transformer.

8. A non-invasive quadratic magnetic resonance local radio frequency prostate coil, comprising:
an electrically conductive loop configured to wrap around a torso of a subject adjacent a pelvic area of the subject;
an electrically conductive coil length connected to a front and a back of the electrically conductive loop and configured to pass between upper thighs of the subject,
whereby the configuration of the electrically conductive coil length and the electrically conductive coil loop create the formation of either an underwear shape, or a thong shape, around the torso of a subject that is adjacent to the pelvic area of the subject;
wherein the conductive loop and the conductive coil length having either an underwear shape, or a thong shape are:
a) detachable from each other;
b) disposable;
c) tuned in order to receive in quadrature magnetic resonance radio frequency signal components when the subject is disposed in a main magnetic field (Bo) orthogonal to an axis of the subject; and
d) generate one or more currents indicative of the received magnetic resonance signal components; and
an interface device that is connected to the connected electrically conductive loop and the electrically conductive coil length having either the underwear shape, or the thong shape; and
wherein the interface device is configured to transmit measures of the one or more currents indicative of the quadrature received magnetic resonance signal components into a signal processing system when the non-invasive quadratic magnetic resonance local radio frequency prostate coil is utilized.

9. The non-invasive quadratic magnetic resonance local radio frequency prostate coil according to claim 8, further including:
a disposable sleeve that is disposed in order to cover the two additional electrically conductive loops.

10. The non-invasive quadratic magnetic resonance local radio frequency prostate coil according to claim 8, wherein the electrically conductive loop and the electrically conductive coil length include at least one of:
thin copper strips; and
thin copper wire, which are compatible with high frequency ultrasound.

11. The non-invasive quadratic magnetic resonance local radio frequency prostate coil according to claim 8, further including: two additional electrically conductive loops connected to the electrically conductive coil length, the two additional electrically conductive loops each being configured to encircle an upper thigh of the subject while being angled toward a waist of the subject.

12. A magnetic resonance system, comprising:
a patient support configured to support a subject horizontally;
a main magnet configured to generate a vertical main magnetic field (Bo) orthogonal to an axis of the subject;
a radio frequency coil disposed adjacent the main magnet with the radio frequency coil being configured to induce magnetic resonance in the subject; and
the non-invasive quadratic magnetic resonance local radio frequency prostate coil according to claim 8.

13. A method of magnetic resonance imaging an upper thigh prostrate region of a subject, comprising:
positioning the subject on a patient support with the subject wearing a non-invasive magnetic resonance local radio frequency prostate coil including:
at least two electrically conductive loops with a front and a back, that are connected and arranged in the form of a thong that passes between the upper thighs of the subject and wraps around a torso of the subject adjacent a pelvic area of the subject,
wherein the at least two electrically conductive loops that are arranged in the form of a thong, are:
a) tuned to receive magnetic resonance radio frequency signals along an axis of the subject, when the subject is disposed in a main magnetic field (Bo) generated by a main field magnet orthogonal to the axis of the subject, and
b) detachably connected to one another via a connection device;
exciting magnetic resonance in the subject and receiving the magnetic resonance radiofrequency signals from the subject with the non-invasive prostate coil;
with a reconstruction processor, reconstructing one or more images from the received magnetic resonance radiofrequency signals; and
at least one of disposing of the electrically conductive loops or disposing of a protective sleeve covering the electrically conductive loops.

14. The method of magnetic resonance imaging an upper thigh prostrate region of a subject according to claim 13, wherein positioning includes disposing each of the electrically conductive loops over a thigh and buttocks region of the subject that is located adjacent the prostate.

15. The method of magnetic resonance imaging an upper thigh prostrate region of a subject according to claim 13, wherein positioning further includes disposing each of the electrically conductive loops over at least a portion of a waist of the subject.

16. The method according to claim 13, wherein receiving includes quadrature coupling of the electrically conductive loops.

17. A magnetic resonance imaging system comprising:
one or more data processors utilized in performing the method of magnetic resonance imaging an upper thigh prostrate region of a subject according to claim 13.

18. A non-transitory computer-readable medium carrying software which controls a magnetic resonance imaging system that when executed or implemented performs the method of magnetic resonance imaging an upper thigh prostrate region of a subject according to claim 13.

19. A non-invasive magnetic resonance local radio frequency prostate coil that is utilized in imaging the upper thighs and pelvic area of a subject comprising:
at least two electrically conductive loops that are tuned to receive magnetic resonance radio frequency signals which occur along an axis of a subject disposed in a main magnetic field Bo that is orthogonal to the axis of the subject,
wherein the at least two electrically conductive loops are arranged in either an underwear shape, or a thong shape or a combination of an underwear shape and a thong shape; while connecting to each other along a length located between the thighs of a subject and a length surrounding an axial portion of the subject,
the at least two electrically conductive loops additionally being detachably connected to one another via a connection device;
a disposable protective sleeve being disposed in order to cover the at least two conductive loops; and
an interface device connected to the at least two electrically conductive loops via the connection device, and
wherein the interface device is configured to transmit measures of the received magnetic resonance radio frequency signals into a signal processing system when the non-invasive magnetic resonance local radio frequency prostate coil is utilized.

* * * * *